(12) United States Patent
Walker et al.

(10) Patent No.: US 7,047,072 B2
(45) Date of Patent: May 16, 2006

(54) SELECTING ELECTROTHERAPY DOSAGE

(75) Inventors: Robert G. Walker, Bothell, WA (US); Joseph L. Sullivan, Kirkland, WA (US)

(73) Assignee: Medtronic Emergency Response Systems, Inc., Redmond, WA (US)

( * ) Notice: Subject to any disclaimer, the term of this patent is extended or adjusted under 35 U.S.C. 154(b) by 513 days.

(21) Appl. No.: 10/314,500

(22) Filed: Dec. 4, 2002

(65) Prior Publication Data

US 2004/0111124 A1  Jun. 10, 2004

(51) Int. Cl.
*A61N 1/39* (2006.01)

(52) U.S. Cl. .............................................. 607/5; 607/8

(58) Field of Classification Search ................. 607/5–8
See application file for complete search history.

(56) References Cited

U.S. PATENT DOCUMENTS

| | | |
|---|---|---|
| 4,840,177 A | 6/1989 | Charbonnier et al. |
| 5,111,813 A | 5/1992 | Charbonnier et al. |
| 5,316,001 A | 5/1994 | Ferek-Petric et al. |
| 5,593,427 A | 1/1997 | Gliner et al. |
| 5,999,852 A | 12/1999 | Elabbady et al. |
| 6,101,413 A | 8/2000 | Olson et al. |
| 6,347,248 B1 | 2/2002 | Gliner |
| 6,374,137 B1 | 4/2002 | Morgan et al. |
| 6,485,437 B1 | 11/2002 | Tapper |
| 6,650,936 B1 | 11/2003 | Sullivan et al. |
| 2002/0052631 A1 | 5/2002 | Sullivan et al. |

FOREIGN PATENT DOCUMENTS

EP    0 277 314 A1    8/1988

OTHER PUBLICATIONS

International Preliminary Examination Report for PCT/US03/38308, filed Dec. 3, 2003 (4 pages).

*Primary Examiner*—Scott M. Getzow
(74) *Attorney, Agent, or Firm*—Shumaker & Sieffert, P.A.

(57) ABSTRACT

A dosage for electrotherapy delivered to a patient, such as a defibrillation pulse delivered by an external defibrillator, is selected based on an age-related classification, such as adult or child, and a measured electrical parameter, such as the transthoracic impedance, of the patient. For example, a nominal voltage level for an energy storage circuit may be determined based on a nominal dosage. The nominal voltage level may be adjusted by applying a function that relates voltage level adjustment to impedance to the measured impedance. The function may be selected based on the age-related classification of the patient. The dosage of the defibrillation pulse delivered based on the adjusted voltage level, i.e., the selected dosage, may have a substantially equivalent probability of success for the patient as the nominal dosage would provide for a reference patient with an average transthoracic impedance for the class of which the patient is a member.

45 Claims, 5 Drawing Sheets

SELECTING ELECTROTHERAPY DOSAGE

TECHNICAL FIELD

The invention relates to medical devices, and more particularly, to medical devices that deliver electrotherapy to a patient.

BACKGROUND

A medical device that delivers electrotherapy to a patient stores energy, and delivers the stored energy to the patient. An external defibrillator, for example, delivers energy to a patient whose heart is undergoing fibrillation and has lost its ability to contract. Ventricular fibrillation is particularly life threatening because activity within the ventricles of the heart is so uncoordinated that virtually no pumping of blood takes place. An electrical pulse delivered to a fibrillating heart may stop the fibrillation and allow it to reestablish a normal sinus rhythm.

An external defibrillator applies a defibrillation pulse via electrodes placed upon the chest of a patient. When a switch is closed, current flows between the electrodes and the defibrillator delivers at least some of the stored energy to the patient. The dosage of energy delivered is generally between 2 and 300 joules. The dosage of energy delivered may be selected by an operator of the external defibrillator, or may be selected by the defibrillator from a preprogrammed progression of dosages. In some cases, the patient may need multiple shocks, and increasing dosages may be delivered with each shock. The dosage of energy delivered when the patient is a child is generally less than when the patient is an adult.

The efficacy of a particular electrotherapy dosage for a particular patient is influenced by physiological characteristics of the patient, such as the transthoracic impedance of the patient. Conventional defibrillators are often specified for and tested with a standard load, such as 50 ohms, that represents the transthoracic impedance of a standard patient. Further, operators of defibrillators often select dosages, and progressions are often preprogrammed based on formulas, tables, or protocols that assume a standard patient with a standard transthoracic impedance. The actual transthoracic impedance of patients, however, can vary greatly in a range from 20 to 300 ohms, though most patients typically fall in a range from 25 to 180 ohms. Further, different classes of patients exhibit different ranges of transthoracic impedances. For example, an average transthoracic impedance for adults is approximately 80 ohms, while an average transthoracic impedance for children is about 60 ohms.

The efficacy of a defibrillation pulse is a function of the current that flows between the electrodes and the width of the defibrillation pulse. The current that flows between the electrodes is a function of the voltage between the electrodes and the transthoracic impedance of the patient. For a given voltage level, a patient having a lower transthoracic impedance than the average will experience a greater current flow than a patient with the average impedance, and a patient having a higher transthoracic impedance than the standard will experience a lesser current flow than a patient with the average impedance. Too little current flow resulting from a defibrillation pulse may not be effective in defibrillating the heart of the patient, while too great a current flow can be inefficient, and more importantly, may damage the tissue of the patient.

SUMMARY

The invention provides techniques for selecting a dosage for electrotherapy to be delivered to a patient. The invention may be embodied in an external defibrillator and the electrotherapy may be a defibrillation pulse delivered by the external defibrillator. The dosage may be an energy level for the defibrillation pulse. In general, a defibrillator selects a dosage based on an age-related classification for a patient, such as adult or child, and a measured electrical parameter, such as the transthoracic impedance, of the patient.

For example, the defibrillator may determine a nominal voltage level for an energy storage circuit of the defibrillator based on a nominal dosage. The defibrillator may receive the nominal dosage from an operator of the defibrillator or select the nominal dosage from a preprogrammed progression of dosages. The defibrillator may adjust the nominal voltage level by applying a function that relates voltage level adjustment and impedance to the measured transthoracic impedance, charge the energy storage circuit to the adjusted voltage level, and deliver a defibrillation pulse at a dosage that is a function of the adjusted voltage level.

The defibrillator may select the function from a plurality of functions stored in a memory based on the age-related classification of the patient. A function that describes a relationship between voltage level adjustment and impedance may be generated for each of a plurality of classifications based on a model that describes a relationship between voltage level, impedance, and cardiac response and the average impedance for patients within the classification. The dosage of the defibrillation pulse delivered based on the adjusted voltage level, i.e., the selected dosage, may have a substantially equivalent probability of success for the patient as the nominal dosage would provide for a reference patient with an average transthoracic impedance for the class of which the patient is a member.

In one embodiment, the invention is directed to a method in which a dosage is selected based on an age-related classification of a patient and a measured electrical parameter of the patient. Electrotherapy is delivered to the patient at the selected dosage. The dosage may be an energy level for a defibrillation pulse, and the electrotherapy delivered may be the defibrillation pulse. The measured electrical parameter may be a measured transthoracic impedance of the patient. The age-related classification may be determined by determining whether the patient is an adult or child.

In another embodiment, the invention is directed to a device that includes a set of electrodes for coupling to a patient, and a measuring circuit that measures an electrical parameter of the patient via the electrodes. The device also includes a processor. The processor selects a dosage based on an age-related classification of the patient and the measured electrical parameter. The processor controls delivery of electrotherapy at the selected dosage to the patient via the electrodes.

In another embodiment, the invention is directed to computer-readable medium that includes program instructions. The instructions cause a programmable processor to select a dosage based on an age-related classification of a patient and a measured electrical parameter of the patient, and control delivery of electrotherapy at the selected dosage to the patient.

In another embodiment, the invention is directed to a method in which an indication of an age-related classification of a patient is received, and an impedance of the patient is measured. One of a set of functions is selectively applied to the measured impedance based on the indicated age-related classification to determine a voltage level adjustment. A nominal defibrillation pulse energy level is identified, and a nominal voltage level is determined based on the nominal defibrillation pulse energy level. The nominal voltage level is adjusted as a function of the determined voltage level adjustment, and a defibrillation pulse is delivered to the patient at an energy level that is a function of the adjusted voltage level.

In another embodiment, the invention is directed to a method in which a model that describes a relationship between voltage level, impedance, and cardiac response is created, and average impedance values for each of a plurality of age-related classifications of patients are determined. A function that describes a relationship between voltage level adjustment and impedance for each of the classifications is determined based on the model and the average impedance for the classification.

In another embodiment, the invention is directed to a method in which a nominal dosage is identified. A dosage is selected based on a measured electrical parameter of a patient that is a child and the nominal dosage to provide a first probability of successful electrotherapy for the patient based on the measured electrical parameter that is substantially equivalent to a second probability of successful electrotherapy provided by the nominal dosage based on an average value for the electrical parameter for children. Electrotherapy is delivered to the patient at the selected dosage.

In another embodiment, the invention is directed to a method in which a nominal dosage is identified and a dosage is selected based on a measured electrical parameter of a patient that is a child and the nominal dosage. A dosage is selected that is greater than the nominal dosage if the measured electrical parameter is greater than an average value of the electrical parameter for children, less than the nominal dosage if the measured electrical parameter is less than the average value, or equal to the nominal dosage if the measured electrical parameter is equal to the average value. Electrotherapy is delivered to the patient at the selected dosage.

The invention can provide one or more advantages, including increasing the probability of successful defibrillation for patients with transthoracic impedances that vary from the average. In addition to increasing the probability of successful defibrillation, the current flow resulting from defibrillation pulses delivered at dosages selected in this manner may not be so great that tissues of patients with low transthoracic impedances are damaged. Further, because dosages are selected based on an age-related classification of the patient, the selected dosages may be more appropriate for patients within a particular class then if the dosages were selected based on transthoracic impedance alone. Selecting dosages based on age-related classifications may further reduce the likelihood that the defibrillation pulses will result in too little or too great a current flow for certain classes of patients, such as children. In some embodiments, it may be possible to achieve a substantially equivalent probability of successful defibrillation for patients with impedances that vary from the average impedance for the class as is achieved by a nominal dosage for patients with average impedance for a class.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
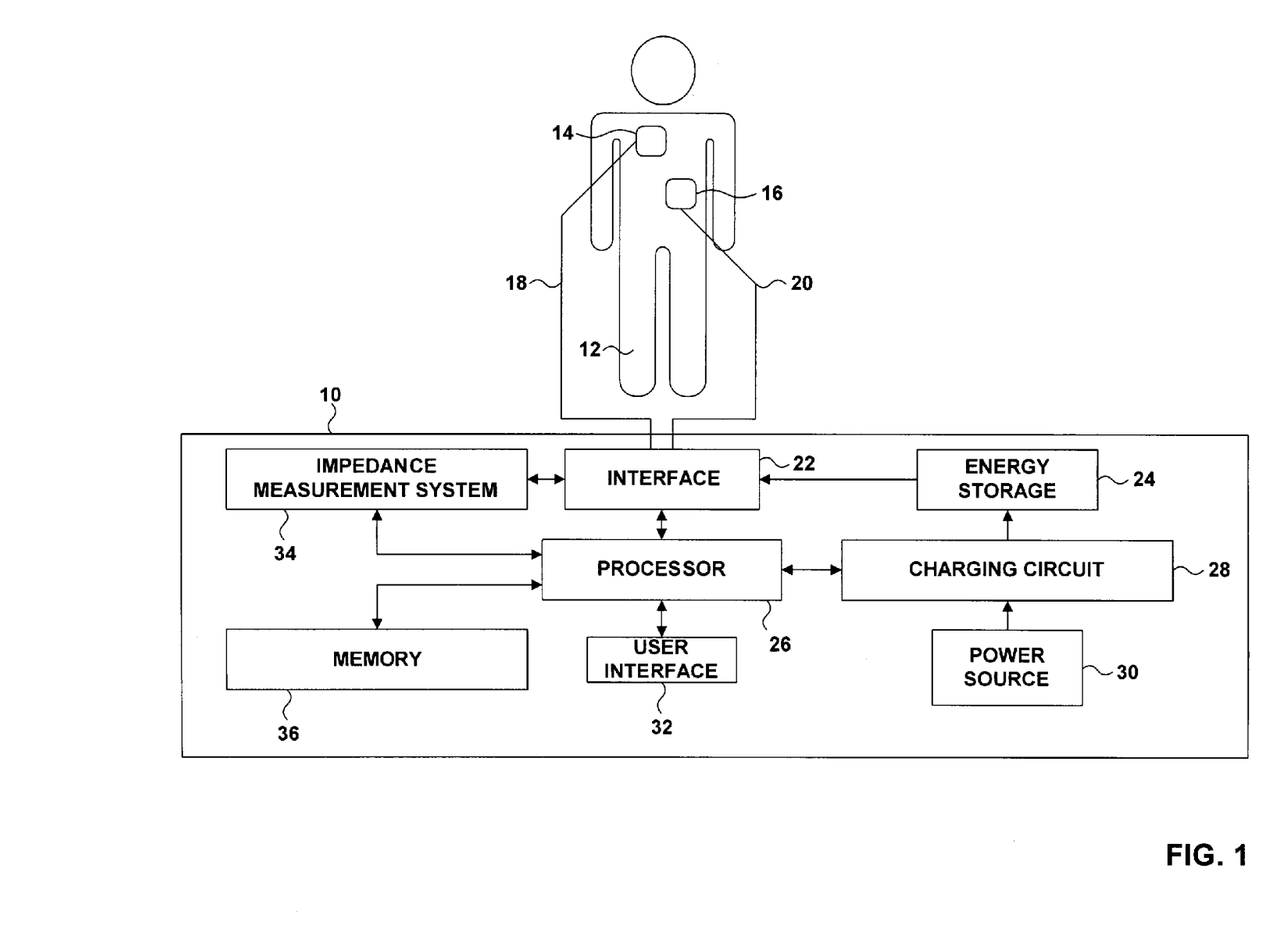
FIG. 1 is a block diagram of an example external defibrillator coupled to a patient in accordance with the invention.

FIG. 1 is a block diagram of an example external defibrillator 10 coupled to a patient 12. Defibrillator 10 administers electrotherapy in the form of defibrillation pulses to patient 12. In some embodiments, as will be described in greater detail below, defibrillator 10 may select a dosage for a defibrillation pulse based on an age-related classification, such as adult or child, and a measured electrical parameter, such as the transthoracic impedance, of patient 12. In some embodiments, defibrillator 10 may select a dosage with the objective of providing an increased probability of successful defibrillation for patient 12 whose transthoracic impedance varies from an average transthoracic impedance for the age-related classification. In some embodiments, it may be possible to achieve a substantially equivalent probability of successful defibrillation for patient 12 as is achieved by a nominal dosage for patients with average impedance for a class. A successful dosage of electrotherapy produces a desired physiological response in patient 12. For example, a successful defibrillation pulse provided by defibrillator 10 depolarizes the heart of patient 12 and allows the heart to reestablish a normal rhythm.

Additionally, the current flow resulting from defibrillation pulses delivered by defibrillator 10 at dosages selected in this manner may be effective in avoiding or reducing damage to patient tissue for a patient 12 with a low transthoracic impedance. Further, because defibrillator 10 selects dosages based on an age-related classification of patient 12, the selected dosages may be more appropriate for patient 12 within a particular class than if defibrillator 10 selected the dosages based on transthoracic impedance alone. Selecting dosages based on age-related classifications may further reduce the likelihood that the defibrillation pulses will result in too little or too great a current flow for certain classes of patients, such as children. In other words, selection of dosages based on age-related classifications may permit more optimal current levels for different patients.

Defibrillator 10 delivers defibrillation pulses to patient 12 via electrodes 14 and 16, which may be hand-held electrode paddles or adhesive electrode pads placed on the skin of patient 12. The body of patient 12 provides an electrical path between electrodes 14 and 16. Electrodes 14 and 16 are coupled to defibrillator 10 via conductors 18 and 20 and interface 22. In a typical application, interface 22 includes a receptacle, and conductors 18 and 20 plug into the receptacle.

Interface 22 includes a switch (not shown) that, when activated, couples an energy storage circuit 24 to electrodes 14 and 16. Energy storage circuit 24 includes components, such one or more capacitors, which store the energy to be delivered to patient 12 via electrodes 14 and 16 as a defibrillation pulse. Before a defibrillation pulse may be delivered to patient 12, energy storage circuit 24 must be charged. A processor 26 directs a charging circuit 28 to charge energy storage circuit 24 to a voltage level that processor 26 determines based on the dosage of energy to be provided to patient 12. Processor 26 may take the form of a microprocessor, digital signal processor (DSP), ASIC, FPGA, or other logic circuitry programmed or otherwise configured to operate as described herein. Charging circuit 28 comprises, for example, a flyback charger that transfers energy from a power source 30 to energy storage circuit 24. Power source 30 may comprise, for example, batteries and/or an adapter to an exterior power source such as an electrical outlet.

Defibrillator 10 may be a manual or automatic external defibrillator. Where defibrillator 10 is a manual defibrillator, an operator of defibrillator 10 may select a nominal dosage, e.g., energy level, for each defibrillation pulse delivered to patient 12. Processor 26 may receive the selection made by the operator via a user interface 32, which may include input devices, such as a keypad, and output devices, such as various indicator lights, a CRT, LED, or LCD screen, and a speaker. Where defibrillator 10 is an automatic defibrillator, processor 26 may select a nominal dosage from a preprogrammed progression of dosages stored in a memory 36 based on number of defibrillation pulses already delivered to patient 12.

In either case, processor 26 may determine the voltage level to charge energy storage circuit 24 to based on the selected nominal dosage, an age-related classification of patient 12, and a measured electrical parameter of patient 12. Processor 26 may, for example, select a desired dosage or adjust the nominal dosage based on the age-related classification and the measured electrical parameter, determine the voltage level based on the selected or adjusted dosage, and charge energy storage circuit 24 to the determined voltage level. As another example, processor 26 may determine a nominal voltage level based on the nominal dosage, adjust the nominal voltage level based on the age-related classification and the measured electrical parameter, and charge energy storage circuit 24 to the adjusted voltage level. In some embodiments of defibrillator 10, such as automatic defibrillator embodiments, processor 26 may not receive or select a nominal dosage, but may instead directly select a dosage to deliver to patient 12 or a voltage level to charge energy storage circuit 24 to based on the age-related classification and the measured electrical parameter.

Processor 26 may select dosages, voltage levels, dosage adjustments, or voltage level adjustments based on measured electrical parameters using functions, such as equations or look-up tables, which relate these values to the electrical parameter. These functions may be stored in memory 36. Memory 36 may include separate functions for each possible age-related classification, and processor 26 may select an appropriate function based on the age-related classification of patient 12. Memory 36 may also include functions that relate dosages to voltage levels, which processor 36 may use to determine voltage levels based on dosages, or dosages based on voltage levels. The functions that relate dosages to voltage levels may be generated based on techniques known in the art, and will depend on the characteristics of the defibrillation pulses delivered by defibrillator 10, such as the width and shape of the pulse.

Memory 36 may also include program instructions that cause processor 26 to select dosages, voltage levels, dosage adjustments, or voltage level adjustments based on age-related classifications and measured electrical parameters, and to perform the other functions ascribed to processor 26 herein, as describe herein. Memory 36 may include any of a variety of electrical, magnetic or optical media, such as a RAM, ROM, CD-ROM, EEPROM, or magnetic disk.

When the energy stored in energy storage circuit 24 reaches the desired voltage level, processor 26 controls user interface 32 to provide an indication to the operator of defibrillator 10 that defibrillator 10 is ready to deliver a defibrillation pulse to patient 12, such as an indicator light or a voice prompt. The defibrillation pulse may be delivered manually or automatically. Where the defibrillation pulse is delivered manually, the operator may direct processor 26 to deliver the defibrillation pulse via the user interface, by, for example pressing a button. In either case, processor 26 activates the switch to electrically connect energy storage circuit 24 to electrodes 14 and 16, and thereby deliver the defibrillation pulse to patient 12.

Processor 26 may modulate the defibrillation pulse delivered to patient 12. Processor 26 may, for example, control the switch to regulate the shape of the waveform of the pulse and the width of the pulse. Processor 26 may control the switch to modulate the pulse to, for example, provide a multiphasic pulse, such as a biphasic truncated exponential pulse, as is known in the art.

Processor 26 may perform other functions as well, such as monitoring electrocardiogram (ECG) signals sensed via electrodes 14 and 16 and received via interface 22. Processor 26 may determine whether the heart of patient 12 is fibrillating based upon the ECG signals in order to determine whether a defibrillation pulse should be delivered to patient 12. Where a defibrillation pulse has already been delivered, processor 26 may evaluate the efficacy of the delivered defibrillation pulse by determining if the heart is still fibrillating in order to determine whether an additional defibrillation pulse is warranted. Processor 26 may automatically control delivery of defibrillation pulses via interface circuit 22 based on these determinations, or may advise the operator of defibrillator 10 of these determinations via user interface 32.

As, described above, processor 26 selects a dosage for a defibrillation pulse to deliver to patient 12 based, in part, on an age-related classification of patient 12. As mentioned above, processor 26 may, for example, classify patient 12 as an adult or a child. Processor 26 may receive an indication of the age-related classification of patient 12 in a number of ways. For example, the operator of defibrillator 10 may determine whether the patient is an adult or a child, and processor 26 may receive an input from the operator indicating the classification via user interface 32.

As another example, processor 26 may detect a type of electrodes 14 and 16 via interface 22, and determine the classification of patient 12 based on the electrode type. Different types of electrodes 14 and 16 may be used by the operator depending on whether patient 12 is an adult or a child. Connectors (not shown) between conductors 18 and 20 and interface 22 may include circuits with a particular resistance that indicates whether electrodes 14 and 16 are for use with adults or children. Processor 26 may direct interface 22 to apply a constant voltage or current to the circuits, and detect the electrode type based on a resulting current or voltage measured by interface 22.

As another example, processor 26 may determine the age-related classification of patient 12 based on a nominal dosage received from the operator of defibrillator 10. In general, operators select lower dosage defibrillation pulses for children than for adults. For example, operators often select a first pulse dosage of 2 Joules/kg for children, while a typical first pulse dosage for an adult is 200 Joules. Processor 26 may compare the nominal dosage to a threshold value stored in memory 36, and identify the patient as an adult or a child based on the comparison. As an example, the threshold value may be approximately 30 Joules.

As discussed above, processor 26 also selects the dosage for a defibrillation pulse to deliver to patient 12 based on a measured electrical parameter of patient 12. As mentioned above, the electrical parameter may be the transthoracic impedance of patient 12. Processor 26 may direct an impedance measurement system 34 to measure the transthoracic impedance of patient 12 via electrodes 14 and 16, receive the measured transthoracic impedance from impedance measurement system 34, and select a dosage based on the measured transthoracic impedance.

Impedance measurement system 34 may employ any of several known impedance measurement techniques to measure the transthoracic impedance of patient 12. For example, system 34 may use a low-level current technique to measure the impedance. Alternatively, or in addition to this technique, system 34 may measure the impedance during delivery of a defibrillation pulse.

Where impedance measurement system 34 employs a low-level current technique, a current source (not shown) of system 34 may generate an "excitation current," also called a "carrier," that is applied to patient 12 through interface 22 and electrodes 14 and 16. The excitation current may be an alternating current signal of known magnitude and frequency. The excitation current is much smaller in magnitude than the defibrillation current delivered during delivery of an energy or current dosage. A typical excitation current has a magnitude of around 100 microamperes. The frequency of the excitation current is generally within a range from 5–100 kHz, and may be approximately 62 kHz.

In such embodiments, impedance measurement system 34 may detect the response to the excitation current as a time-varying voltage difference between electrodes 14 and 16. System 34 may include amplifiers, filters, and the like (not shown) to detect the voltage difference and process the resulting signal, and an analog-to-digital filter (not shown) to convert the signal to a digital signal. A controller (not shown) of system 34 that is responsive to signals received from processor 26 may control the current source, measure the magnitude and phase of the voltage difference in order to measure the impedance of patient 12, and provide the measured transthoracic impedance to processor 26. Alternatively, the controller may be embodied within processor 26.

Impedance measurement system 34 may measure the transthoracic impedance of patient 12 during delivery of a defibrillation pulse in several ways. For example, system 34 may detect the current flow between electrodes 14 and 16 resulting from the delivery of the defibrillation pulse, and calculate the impedance based on the magnitude and phase of the detected current flow and the voltage waveform of the defibrillation pulse delivered to patient 12. As another example, system 34 may analyze the drop in the voltage stored in energy storage circuit 24 over a period of time during the delivery of the defibrillation pulse. Given a known capacitance and resistance internal to defibrillator 10, the transthoracic impedance of patient 12 can be determined based on the contribution of the impedance of patient 12 to the voltage rate of decay of energy storage circuit 24.

Impedance measurement system 34 may measure the transthoracic impedance during previously delivered pulses, and use one or more of the measured impedances to select a dosage for a current defibrillation pulse. In some embodiments, processor 26 may select a dosage for a current pulse based on an impedance measured by system 34 during the delivery of a previous pulse, and direct energy storage circuit 24 and/or interface 22 to adjust the voltage amplitude of a subsequent pulse based on the selected dosage. In some embodiments, processor 26 may select the dosage based on multiple impedances measured by any of the above-discussed techniques in an effort to compensate for inaccuracies of deficiencies of any one of the techniques. Processor 26 may, for example, determine the average of impedances measured at various times using various techniques, and use the average to select the dosage.

As discussed above, processor 26 may select the dosage based on the measured impedance of patient 12 by comparing the measured impedance to a function, such as an equation or look-up table, stored in memory 36, which is selected by processor 26 based on the age-related classification of patient 12. The function may relate dosages, voltage levels, dosage adjustments, or voltage level adjustments to impedance, as discussed above. The function may have been generated such that the dosage of the defibrillation pulse delivered by processor 26 based on the dosage, voltage level, dosage adjustment, or voltage level adjustment selected by processor 26 has a substantially equivalent probability of success for patient 12 as a nominal dosage would provide for a reference patient with an average transthoracic impedance for the age-related classification of patient 12.

Figure 2:
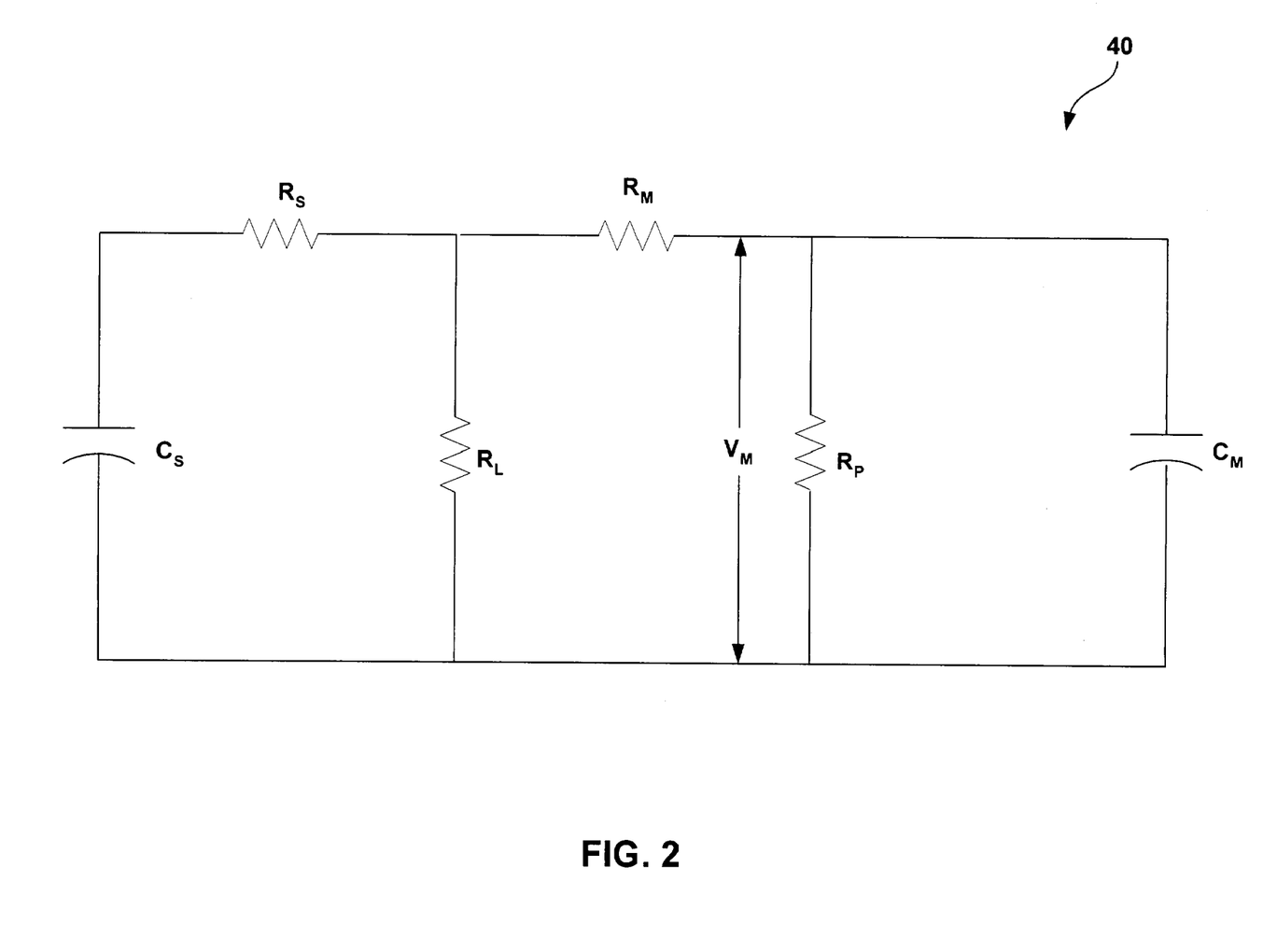
FIG. 2 is a circuit diagram of an example defibrillator/patient system model that an external defibrillator may use to select a dosage for a defibrillation pulse based on an age-related classification and a measured transthoracic impedance of a patient.

FIG. 2 is a circuit diagram of an example defibrillator/patient system model 40 that processor 26 of defibrillator 10 may use to select a dosage for a defibrillation pulse based on an age-related classification and a measured transthoracic impedance of patient 12. In model 40, the electrical characteristics of defibrillator 10 are represented by capacitor $C_S$, which represents the capacitance of energy storage circuit 24, in series with resistance $R_S$, which represents the internal impedance of defibrillator 10. The electrical characteristics of a model patient are represented by resistance $R_L$, which represents the transthoracic impedance of the model patient, and a resistor-capacitor (RC) circuit, which includes resistances $R_M$ and $R_P$ and a capacitance $C_M$, and represents the electrical characteristics of a cell in the myocardium of the model patient.

The probability of success of a defibrillation pulse is generally dependent on the voltage that develops across the myocardial cells of a patient when the pulse is delivered to the patient. A voltage $V_M$ across resistance $R_P$ and a capacitance $C_M$ may be calculated using known circuit analysis techniques, and represents the voltage that develops across the model cardiac cell membrane, i.e., the cardiac model response, when electrical energy is delivered to the model patient from the capacitance $C_S$. Processor 26 may use model 40 to select a dosage for a defibrillation pulse by selecting a dosage that yields equivalent values of $V_M$ for both patients. In some embodiments, the dosage selected may provide a substantially equivalent probability of successful defibrillation for patient 12 as a nominal dosage would provide for a reference patient with an average transthoracic impedance.

In particular, processor 26 may calculate a voltage level of capacitance $C_S$ corresponding to the nominal dosage, and calculate first voltage $V_M$ resulting from the discharge of capacitance $C_S$ with the resistance $R_L$ set at the average transthoracic impedance for the age-related classification of patient 12. Processor may then determine a voltage level of capacitance $C_S$ that yields a second voltage $V_M$ equal to the first voltage $V_M$ with the resistance $R_L$ set at the measured transthoracic impedance of patient 12. Processor 26 may calculate a desired dosage based on the second voltage $V_M$, or may simply charge energy storage circuit 24 to the second voltage $V_M$.

Instead of selecting dosages or voltage levels by applying model 40 at the time of treatment of each patient, in some embodiments, processor 26 may, as discussed above, select the dosage by comparing the measured impedance to a function, such as an equation or look-up table, stored in memory 36. For example, functions that relate dosages, voltage levels, dosage adjustments, or voltage level adjustments to impedance for each possible age-related classification of patients may be generated before use of defibrillator 10 using model 40. The functions may be generated using a device separate from defibrillator 10, such as a personal computer, workstation, or the like.

One or more functions that relate dosage or voltage level to measured impedance for a particular age-related class of patients may be generated using model 40 by identifying the values of $V_M$ produced by a variety of nominal dosage or voltage levels for a patient with average impedance for the class. The dosages or voltage levels that produce values of $V_M$ equal to the nominal values of $V_M$ for a variety of possible measured impedances may then be determined for each nominal dosage or voltage level in the manner described above. One or more equations or look-up tables that describe the relationship between nominal dosages or voltage levels, impedance, and desired dosages or voltage levels may be generated and stored in memory 36 for the class. The process may be repeated for multiple classes of patients using different average impedance values for each class.

Model 40 may also be more preferably used to generate functions for each age-related class of patients that relate adjustments to be made to nominal dosages or voltage levels to impedance, as will be described with reference to FIG. 3. The adjustment provided by such a function for a particular measured impedance may be applied to any nominal dosage or voltage level. The generation of such a function may be less complicated than the generation of functions that relate desired dosages or voltage levels directly to impedance and nominal dosages or voltage levels because a corresponding dosage/voltage level need not be calculated for each nominal dosage/voltage level and impedance combination. Existing defibrillators generally calculate a nominal voltage level from a nominal dosage, and charge an energy storage circuit to the nominal voltage level. Such defibrillators may be modified to use such a function to determine an adjustment to the nominal voltage level, and charge the energy storage circuit to the adjusted voltage level in order to deliver a defibrillation pulse with the desired probability of success.

Figure 3:
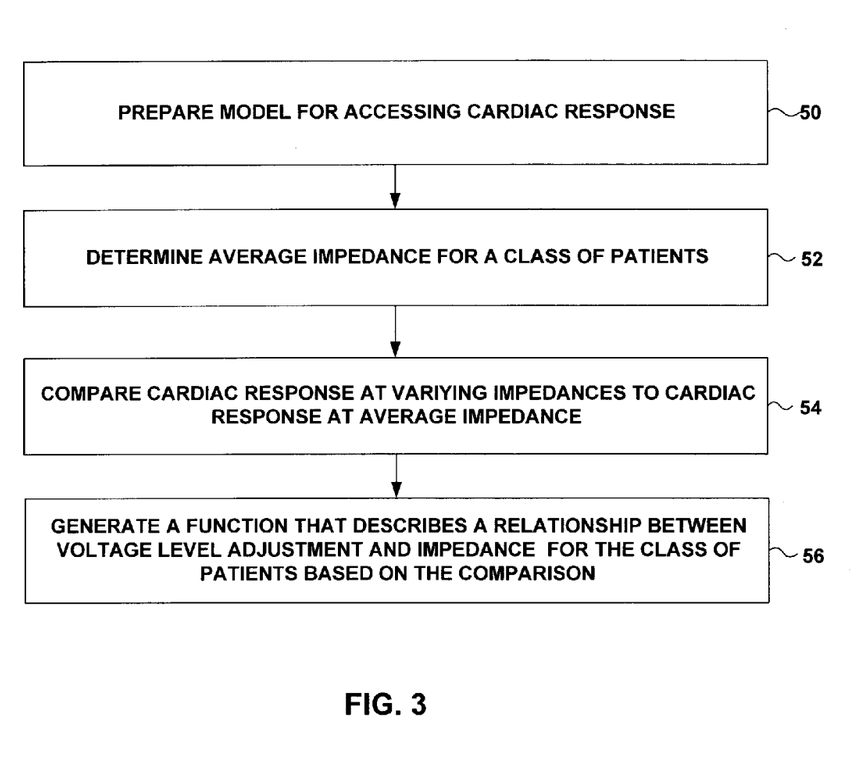
FIG. 3 is a flow diagram illustrating an example method for generating functions that describe relationships between dosage or voltage level adjustment and transthoracic impedance using a defibrillator/patient system model.

FIG. 3 is a flow diagram illustrating an example method for generating functions that describe relationships between dosage or voltage level adjustment and transthoracic impedance using a defibrillator/patient system model. A model, such as model 40, may be prepared for accessing the cardiac response of patients to defibrillation therapy, as described above (50). The cardiac response of a patient with a particular transthoracic impedance to a particular voltage level of capacitance $C_S$ may be assessed by calculating the voltage $V_M$ using model 40, as described above.

A function that provides dosage or voltage level adjustments based on measured transthoracic impedance may be generated for each of a number of age-related classes of patients. For example, a first function may be generated for adults, and a second function may be generated for children. In order to generate a function for a particular class, the average transthoracic impedance of the class is determined (52).

Model 40 is used to compare the cardiac response at a variety of impedances to the cardiac response at the average impedance for the class (54). Based on the comparison, a function that describes a relationship between voltage level adjustment and impedance may be generated for the class of patients (56). For example, using model 40 and known circuit analysis techniques, an equation that describes $V_M$ as a function of transthoracic impedance, among other things, may be derived. An equation that describes the voltage level adjustment necessary to equate voltage $V_M$ at any value of the transthoracic impedance to voltage $V_M$ at the average impedance may be expressed as a ratio between a first equation that describes $V_M$ with variable transthoracic impedance and a second equation that describes $V_M$ with at the average transthoracic impedance, which is a constant value for the class.

The equation that describes the voltage level adjustment as a function of transthoracic impedance may be used as the function for the class, or a look-up table may be generated by applying the equation to discrete impedance values. The equation may be stored in memory 36 of defibrillator 10. The equation does not depend on a particular nominal voltage level, and thus may be selected by processor 26 to adjust any nominal voltage level based on a measured transthoracic impedance of patient, and applied to the nominal voltage level by multiplying the nominal voltage level by the adjustment. The equation may be converted to an equation that relates dosage adjustments to impedance using any of the known techniques for converting a voltage level to a dosage. A similar equation may be generated for each age-related class of patients using a different value for the average impedance for each class, and stored in memory 36. Processor 26 may select the appropriate equation based on the age-related classification of patient 12, which may be determined as described above.

Figure 4:
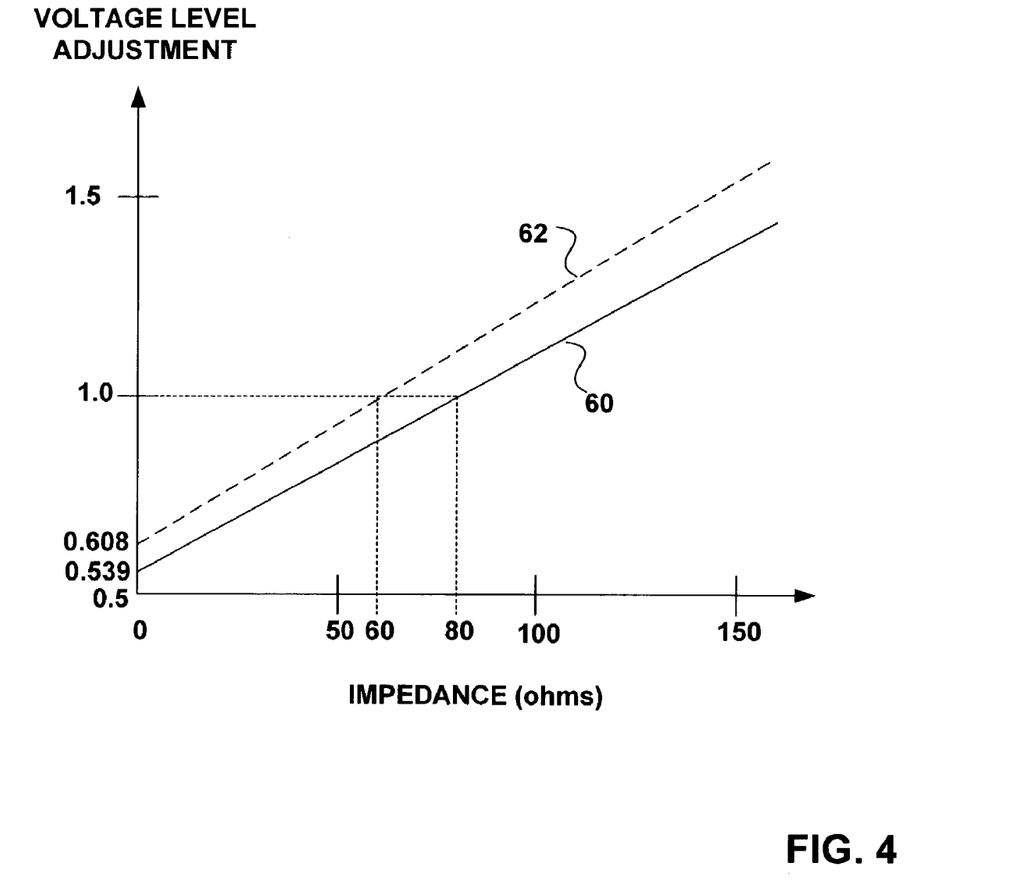
FIG. 4 is a graph illustrating example functions that describe relationships between voltage level adjustment and transthoracic impedance.

FIG. 4 is a graph illustrating example functions that describe relationships between voltage level adjustment and transthoracic impedance. The functions illustrated may be used by processor 26 of defibrillator 10 to adjust a nominal voltage level based on a measured transthoracic impedance of patient 12. Curves 60 and 62 are graphical depictions of equations that describe voltage level adjustment as a function of transthoracic impedance.

The equations depicted by curves 60 and 62 may have been generated as described above with reference to FIG. 3. Although curves 60 and 62 are linear, equations generated as described above may not be linear. Linear or nonlinear equations may be used by processor 26 to select voltage level adjustments based on measured impedances. In some embodiments, a best-fit linear approximation of a nonlinear equation may be calculated and used to select voltage level adjustments based on measured impedances.

Where both of the equations depicted by curves 60 and 62 are stored in memory 36, processor 26 may select one of the equations based on the age-related classification of patient 12. Curve 60 may, for example, correspond to an equation generated as described above using an average transthoracic impedance value for an adult, e.g., 80 ohms. Curve 62 may, for example, correspond to an equation generated as described above using an average transthoracic impedance value for a child, e.g., 60 ohms. Thus, processor 26 may select the equation corresponding to curve 60 if processor 26 determines that patient 12 is an adult, and select the equation corresponding to curve 62 if processor 26 determines that patient 12 is a child.

The equations depicted by curves 60 and 62 may respectively be described as: ADJUSTMENT=0.0058*MEASURED IMPEDANCE+ 0.539; and ADJUSTMENT=0.0065*MEASURED IMPEDANCE+0.608. Processor 26 may calculate a value for a voltage level adjustment using either curve and the measured transthoracic impedance of patient 12. Processor may multiply a nominal voltage level, which may be determined based on a nominal dosage, by the calculated voltage adjustment to produce an adjusted voltage level, and charge energy storage circuit 24 to the adjusted voltage level. These equations are merely exemplary.

As illustrated in FIG. 4, the equations depicted by curves 60 and 62 produce a voltage level adjustment of 1 when applied to the average impedance value for adults, e.g., 80 ohms, and children, e.g., 60 ohms, respectively. In other words, if the measured transthoracic impedance of patient 12 is equal to the average transthoracic impedance for the age-related class of patients within which patient 12 is classified, the nominal voltage level need not be adjusted because the nominal voltage level corresponds to the desired and expected probability of success for a defibrillation pulse delivered to patient 12. On the other hand, as illustrated in FIG. 4, if the measured impedance of patient 12 is greater or less than the average impedance, processor 26 will adjust the nominal voltage level upward or downward via multiplication with the adjustment value. In some embodiments, these adjustments may provide a probability of successful defibrillation that is similar or substantially equivalent to the desired and expected probability. The dosage of the defibrillation pulse will also increase or decrease based on this adjustment.

As illustrated by FIG. 4, equations generated as described with reference to FIG. 3 vary depending and the average impedance value used. By selecting an equation generated for a particular age-based class of patients, processor 26 of defibrillator 10 may advantageously adjust nominal voltage levels to deliver defibrillation pulses to patients of particular classes that are more appropriate for patients of that those classes than would be delivered if a single equation was used for all patients. For, example, depending on the impedance of a child, the current flow through the child resulting from an adjusted voltage level determined using a single equation that applies to all patients without regard to age-related class may be too low to cause an adequate voltage across myocardial cells and defibrillate the heart, or so high that the tissue of the child may be damaged.

Figure 5:
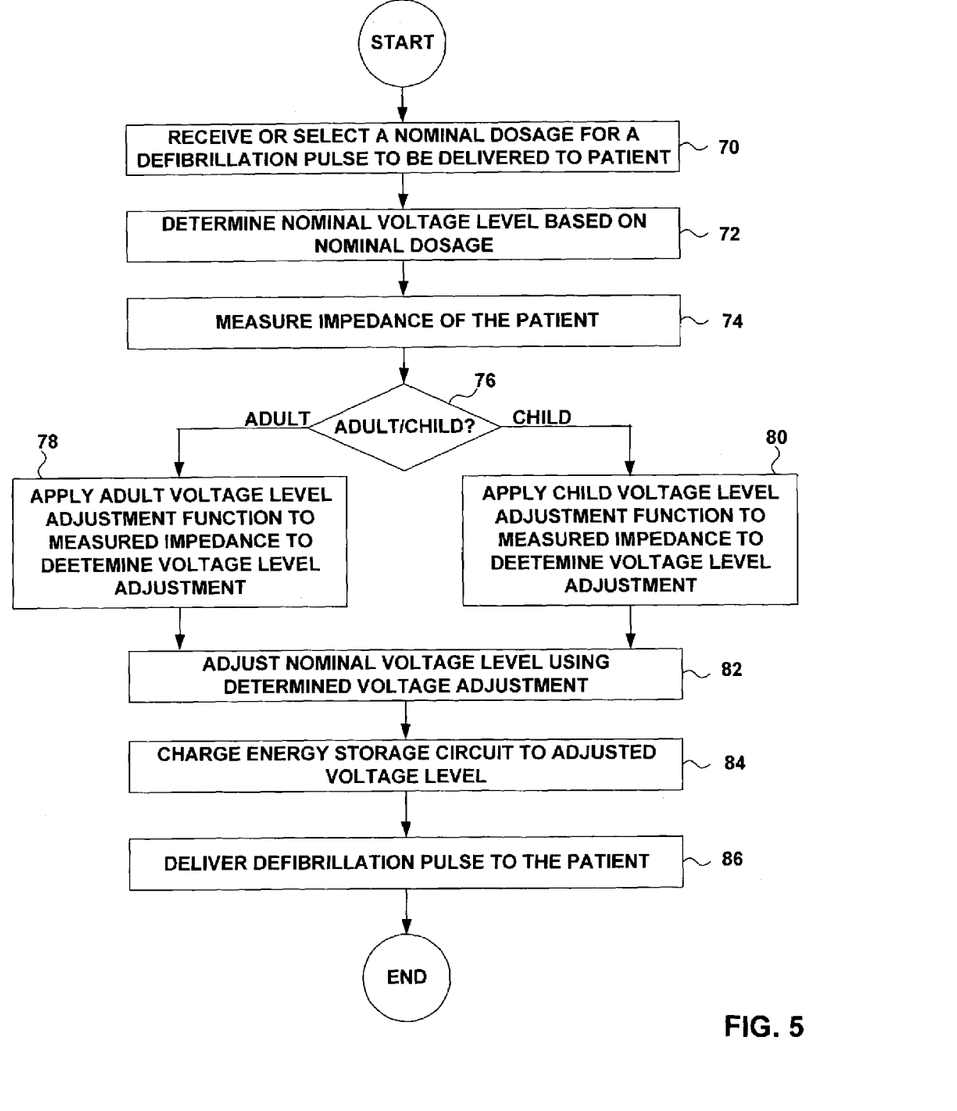
FIG. 5 is a flow diagram illustrating an example method that may be employed by an external defibrillator to select a dosage for a defibrillation pulse based on an age-related classification and a measured transthoracic impedance of a patient in accordance with the invention.

FIG. 5 is a flow diagram illustrating an example method that may be employed by defibrillator 10 to select a dosage for a defibrillation pulse based on an age-related classification and a measured transthoracic impedance of patient 12. Processor 26 of defibrillator 10 may receive or select a nominal dosage, e.g., energy level, for a defibrillation pulse to be delivered to patient 12 (70), and determine a nominal voltage level based on the nominal dosage (72) as described above. Processor 26 may control impedance measurement system 34 to measure the transthoracic impedance of patient 12 using any of the techniques at any of the times described above (74), and receive the measured impedance from system 34.

Processor 26 may also receive an indication of the age-related classification of patient 12 in any of the ways described above. Processor 26 may, for example, determine whether patient 12 is an adult of child based on the indication (76). Memory 36 may include a function that describes a relationship between voltage level adjustment and impedance that is generated based on an average impedance for adults, and a function that describes a relationship between voltage level adjustment and impedance that is generated based on an average impedance for children. The functions may be generated as described above. Processor 26 may select either the adult or child voltage level adjustment function to the measured impedance based on the determination of whether patient 12 is an adult or child, and apply the selected function to the measured impedance to determine a voltage level adjustment as described above (78,80).

Processor 26 may adjust the nominal voltage level using the determined voltage level adjustment by, for example, multiplying the nominal voltage level by the determined adjustment (82). Processor 26 may then direct charging circuit 28 to charge energy storage circuit 24 to the adjusted voltage level (84), and, when energy storage circuit 24 is charged to the adjusted voltage level, may activate the switch within interface 22 or provide an indication to an operator to deliver the defibrillation pulse to patient 12 via electrodes 14 and 16 (86). In some embodiments, in order to decrease the time needed to reach the adjusted voltage level, processor 26 may direct charging circuit 28 to begin charging energy storage circuit 24 to the nominal voltage level upon the determination of the nominal voltage level. Upon the determination of the adjusted voltage level, processor 26 may either direct charging circuit 28 to continue to charge energy storage circuit, or direct at least one of charging circuit 28 and interface 22 to reduce the charge stored in energy storage circuit 24 as necessary to reach the adjusted voltage level.

In situations where processor 26 determines that patient 12 is a child based on a comparison of a nominal dosage received from an operator of defibrillator 10 for a first defibrillation pulse to a threshold value stored in memory 36, processor 26 may continue to apply the child function to subsequent nominal voltage levels determined based on subsequent nominal dosages received from the operator for subsequent defibrillation pulses intended for patient 12 without comparing the subsequent nominal dosages to the threshold value. This may be desirable, as the subsequent nominal dosages may exceed the threshold value. Processor 26 may determine whether subsequent nominal dosages are intended for the same patient by, for example, starting a timer upon the delivery of the first pulse and determining whether the timer has expired before a second nominal dosage is received. The timer may be reset after each defibrillation pulse is delivered to patient 12.

Processor 26 may alternatively determine whether subsequent nominal dosages are intended for the same patient by determining whether electrodes 14 and 16 have been removed to be changed. Connectors for electrodes 14 and 16 may include circuits with resistances, as described above. Processor 26 may receive a signal from interface 22 indicating that a circuit, which is normally closed by the connector circuit, is open during the changing of electrodes 14 and 16.

A number of embodiments of the invention have been described. However, the invention is not limited to the described embodiments. For example, although the invention has been describe herein as embodied in an external defibrillator that delivers electrotherapy to a patient in the form of defibrillation pulse, the invention may be embodied in a variety of medical devices that deliver a variety of electrotherapies to patients. For example, the invention may be embodied in a device that is implanted within a patient, or a device that delivers cardioversion therapy to the patient. The invention may therefore, be embodied in an implanted pacemaker-cardioverter-defibrillator (PCD).

Although age-related classifications of patients have been described herein as one of adult or child, the invention is not so limited. Embodiments of the invention may select a dosage as described herein based on any number of possible age-related classifications. For example, patients may be classified as infant, toddler, child, young adult, adult, and elderly. Functions may be generated for any of these classes of patients as described herein using an average transthoracic impedance value for the class.

Further, although the invention has been described herein as selecting a dosage based on a measured transthoracic impedance of a patient, a variety of electrical parameters may be used by embodiments of the invention. For example, embodiments of the invention may analyze the ECG of the patient sensed via electrodes to determine the rate, or other characteristics, of the fibrillation waveform, and select and apply a function that relates the rate to a dosage, voltage level, dosage adjustment, or voltage level adjustment based on the age-related classification of the patient.

In some embodiments, clinical data may be used instead of or in addition to a defibrillator/patient system model to generate functions that relate dosage, voltage level, dosage adjustment, or voltage level adjustment to the measure electrical parameter. These and other embodiments are within the scope of the following claims.

The invention claimed is:

1. A method comprising:
   receiving a nominal dosage selected by a user;
   determining an age-related classification of a patient based on the nominal dosage;
   selecting a dosage based on the age-related classification and a measured electrical parameter of the patient; and
   delivering electrotherapy at the selected dosage to the patient.

2. The method of claim 1, in which determining an age-related classification of a patient comprises determining whether the patient is one of a child and an adult based on the nominal dosage.

3. The method of claim 1, in which determining the age-related classification based on the nominal dosage comprises:
   comparing the nominal dosage to a threshold value; and
   identifying the patient as one of a child and an adult based on the comparison.

4. The method of claim 3, in which the threshold value is approximately 30 joules.

5. The method of claim 1, in which selecting a dosage comprises
   adjusting the nominal dosage based on the age-related classification and the measured electrical parameter.

6. The method of claim 5, in which adjusting the nominal dosage comprises:
   determining a nominal voltage level based on the nominal dosage;
   adjusting the nominal voltage level; and
   charging an energy storage circuit to the adjusted voltage level.

7. The method of claim 6, in which adjusting the nominal voltage level comprises:
   selecting one of a set of functions that describe relationships between the electrical parameter and voltage level adjustment based on the age-related classification;
   applying the selected function to the measured electrical parameter to determine a voltage level adjustment; and
   adjusting the nominal voltage level as a function of the determined voltage adjustment.

8. The method of claim 7, in which selecting one of a set of functions comprises selecting one of a set that includes at least one of equations and look-up tables.

9. The method of claim 7, in which selecting one of a set of functions comprises:
   determining whether the patient is one of a child and an adult; and
   selecting one of a first function and a second function from the set based on the determination.

10. The method of claim 7, in which the patient comprises a first patient, the nominal dosage comprises a first nominal dosage, and the electrotherapy delivered to the patient comprises a first electrotherapy, the method further comprising:
    receiving a second nominal dosage from the user;
    determining whether a current patient is the first patient;
    applying the selected function to adjust the second nominal dosage based on the determination; and
    delivering a second electrotherapy at the adjusted second dosage to the current patient.

11. The method of claim 5, in which selecting a dosage comprises selecting a dosage to provide a first probability of successful electrotherapy for the patient based on the measured electrical parameter that is substantially equivalent to a second probability of successful electrotherapy provided by the nominal dosage based on an average value for the electrical parameter that corresponds to the age-related classification of the patient.

12. The method of claim 5, in which selecting a dosage comprises selecting a dosage that is one of greater than the nominal dosage if the measured electrical parameter is greater than an average value of the electrical parameter for the age-related classification, less than the nominal dosage if the measured electrical parameter is less than the average value, and equal to the nominal dosage if the measured electrical parameter is equal to the average value.

13. The method of claim 1, in which selecting a dosage comprises selecting an energy level for a defibrillation pulse, and delivering electrotherapy comprises delivering the defibrillation pulse.

14. The method of claim 1, in which the measured electrical parameter comprises a measured transthoracic impedance.

15. A device comprising:
    a set of electrodes for coupling to a patient;
    a measuring circuit that measures an electrical parameter of the patient via the electrodes;
    a user interface; and
    a processor to receive a nominal dosage selected by a user via the user interface, determine an age-related classification of the patient based on the nominal dosage, select a dosage based on the age-related classification of the patient and the measured electrical parameter, and control delivery of electrotherapy at the selected dosage to the patient via the electrodes.

16. The device of claim 15, in which the processor determines whether the patient is one of a child and an adult.

17. The device of claim 15, further comprising a memory to store a threshold value, wherein the processor determines the age-related classification of the patient by comparing the nominal dosage to the threshold value and identifying the patient as one of a child and an adult based on the comparison.

18. The device of claim 17, in which the threshold value is approximately 30 joules.

19. The device of claim 15, in which the processor selects the dosage by adjusting the nominal dosage based on the age-related classification and the measured electrical parameter.

20. The device of claim 19, further comprising an energy storage circuit to store energy for delivery of the electrotherapy to the patient, wherein the processor adjusts the nominal dosage by determining a nominal voltage level that corresponds to the nominal dosage, adjusting the nominal voltage level, and controlling the charging of the energy storage circuit to the adjusted voltage level.

21. The device of claim 20, further comprising a memory to store a set of functions that describe relationships between voltage level adjustment and the electrical parameter, wherein the processor adjusts the nominal voltage level by selecting one of the set of functions based on the age-related classification of the patient, applying the selected function to the measured electrical parameter to determine a voltage level adjustment, and adjusting the nominal voltage level as a function of the determined voltage level adjustment.

22. The device of claim 21, in which the set of functions within the memory includes at least one of equations and look-up tables.

23. The device of claim 21, in which the processor selects one of a set of functions by determining whether the patient is one of a child and an adult and selecting one of a first function and a second function based on the determination.

24. The device of claim 21, in which the patient comprises a first patient, the nominal dosage comprises a first nominal dosage, the electrotherapy delivered to the patient comprises a first electrotherapy, and the processor receives a second nominal dosage selected by the user via the user interface, determines whether a current patient is the first patient, applies the selected function to adjust the second nominal dosage based on the determination, and controls the delivery of a second electrotherapy at the adjusted second nominal dosage to the current patient.

25. The device of claim 19, in which the processor selects the dosage to provide a first probability of successful electrotherapy for the patient based on the measured electrical parameter that is substantially equivalent to a second probability of successful electrotherapy provided by the nominal dosage based on an average value for the electrical parameter that corresponds to the age-related classification of the patient.

26. The device of claim 19, in which the processor selects a dosage by selecting a dosage that is one of greater than the nominal dosage if the measured electrical parameter is greater than an average value of the electrical parameter for the age-related classification, less than the nominal dosage if the measured electrical parameter is less than the average value, and equal to the nominal dosage if the measured electrical parameter is equal to the average value.

27. The device of claim 15, in which the device comprises an external defibrillator, the processor selects a dosage by selecting an energy level for a defibrillation pulse, and the processor delivers electrotherapy by delivering the defibrillation pulse.

28. The device of claim 15, in which the measuring circuit comprises an impedance measuring circuit, and the measured electrical parameter comprises a measured transthoracic impedance.

29. A computer-readable medium comprising instructions that cause a processor to:
receive a nominal dosage selected by a user;
determine an age-related classification of a patient based on the nominal dosage;
select a dosage based on the age-related classification and a measured electrical parameter of the patient; and
control the delivery of electrotherapy at the selected dosage to the patient.

30. The computer-readable medium of claim 29, in which the instructions that cause a processor to determine an age-related classification of a patient comprise instructions that cause a processor to determine whether the patient is one of a child and an adult based on the received nominal dosage.

31. A method comprising:
creating a model that describes a relationship between voltage level, impedance, and cardiac response;
determining average impedance values for each of a plurality of age-related classifications of patients; and
determining a function that describes a relationship between voltage level adjustment and impedance for each of the classifications based on the model and the average impedance for the classification.

32. The method of claim 31, further comprising:
storing a set of the determined functions in memory;
receiving an indication of an age-related classification of a patient;
selecting one of the set of functions based on the indicated age-related classification;
measuring an impedance of the patient;
applying the selected function to the measured impedance to determine a voltage level adjustment;
identifying a nominal defibrillation pulse energy level;
determining a nominal voltage level that corresponds to the nominal defibrillation pulse energy level;
adjusting the nominal voltage level as a function of the determined voltage level adjustment
delivering a defibrillation pulse at an energy level that is a function of the adjusted voltage level to the patient.

33. The method of claim 32, in which the set includes a first functions for children and a second function for adults, receiving an indication of an age-related classification of a patient comprises determining whether the patient is one of a child and an adult, and selecting a function comprises selecting one of the first and second function based on the determination.

34. A method comprising:
identifying a nominal dosage;
selecting a dosage based on a measured electrical parameter of a patient that is a child and the nominal dosage to provide a first probability of successful electrotherapy for the patient based on the measured electrical parameter that is substantially equivalent to a second probability of successful electrotherapy provided by the nominal dosage based on an average value for the electrical parameter for children; and
delivering electrotherapy at the selected dosage to the patient.

35. The method of claim 34, in which selecting a dosage comprises selecting an energy level for a defibrillation pulse, and delivering electrotherapy comprises delivering the defibrillation pulse.

36. The method of claim 34, in which the measured electrical parameter comprises a measured transthoracic impedance.

37. A method comprising:
identifying a nominal dosage;
selecting a dosage based on a measured electrical parameter of a patient that is a child and the nominal dosage; and
delivering electrotherapy at the selected dosage to the patient, in which selecting a dosage comprises selecting a dosage that is one of greater than the nominal dosage if the measured electrical parameter is greater than an average value of the electrical parameter for children, less than the nominal dosage if the measured electrical parameter is less than the average value, and equal to the nominal dosage if the measured electrical parameter is equal to the average value.

38. The method of claim 37, in which selecting a dosage comprises selecting an energy level for a defibrillation pulse, and delivering electrotherapy comprises delivering the defibrillation pulse.

39. The method of claim 37, in which the measured electrical parameter comprises a measured transthoracic impedance.

40. A method comprising:
identifying a nominal dosage;
adjusting the nominal dosage based on an age-related classification of a patient and a measured electrical parameter of the patient; and
delivering electrotherapy at the adjusted dosage to the patient,
wherein adjusting the nominal dosage comprises:
determining a nominal voltage level based on the nominal dosage;
adjusting the nominal voltage level; and
charging an energy storage circuit to the adjusted voltage level,
wherein adjusting the nominal voltage level comprises:
selecting one of a set of functions that describe relationships between the electrical parameter and voltage level adjustment based on the age-related classification;
applying the selected function to the measured electrical parameter to determine a voltage level adjustment; and
adjusting the nominal voltage level as a function of the determined voltage level adjustment, and
wherein the patient comprises a first patient, the nominal dosage comprises a first nominal dosage, and the electrotherapy delivered to the patient comprises a first electrotherapy, the method further comprising:
identifying a second nominal dosage;
determining whether a current patient is the first patient;
applying the selected function to adjust the second nominal dosage based on the determination; and
delivering a second electrotherapy at the adjusted second dosage to the current patient.

41. A method comprising:
identifying a nominal dosage;
adjusting the nominal dosage based on an age-related classification of a patient and a measured electrical parameter of the patient; and
delivering electrotherapy at the adjusted dosage to the patient,
wherein adjusting the nominal dosage comprises adjusting the nominal dosage to provide a first probability of successful electrotherapy for the patient based on the measured electrical parameter that is substantially equivalent to a second probability of successful electrotherapy provided by the nominal dosage based on an average value for the electrical parameter that corresponds to the age-related classification of the patient.

42. A method comprising:
identifying a nominal dosage;
adjusting the nominal dosage based on an age-related classification of a patient and a measured electrical parameter of the patient; and
delivering electrotherapy at the adjusted dosage to the patient,
wherein adjusting the nominal dosage comprises adjusting the nominal dosage to an adjusted dosage that is greater than the nominal dosage if the measured electrical parameter is greater than an average value of the electrical parameter for the age-related classification, less than the nominal dosage if the measured electrical parameter is less than the average value, and equal to the nominal dosage if the measured electrical parameter is equal to the average value.

43. A device comprising:
a set of electrodes for coupling to a patient;
a measuring circuit that measures an electrical parameter of the patient via the electrodes; and
a processor to select a dosage based on an age-related classification of the patient and the measured electrical parameter, and control delivery of electrotherapy at the selected dosage to the patient via the electrodes,
wherein the processor selects a dosage by identifying a nominal dosage and adjusting the nominal dosage based on the age-related classification and the measured electrical parameter,
the device further comprising an energy storage circuit to store energy for delivery of the electrotherapy to the patient, wherein the processor adjusts the nominal dosage by determining a nominal voltage level that corresponds to the nominal dosage, adjusting the nominal voltage level, and controlling the charging of the energy storage circuit to the adjusted voltage level,
the device further comprising a memory to store a set of functions that describe relationships between voltage level adjustment and the electrical parameter, wherein the processor adjusts the nominal voltage level by selecting one of the set of functions based on the age-related classification of the patient, applying the selected function to the measured electrical parameter to determine a voltage level adjustment, and adjusting the nominal voltage level as a function of the determined voltage level adjustment, and
wherein the patient comprises a first patient, the nominal dosage comprises a first nominal dosage, the electrotherapy delivered to the patient comprises a first electrotherapy, and the processor identifies a second nominal dosage, determines whether a current patient is the first patient, applies the selected function to adjust the second nominal dosage based on the determination, and controls the delivery of a second electrotherapy at the adjusted second nominal dosage to the current patient.

44. A device comprising:
a set of electrodes for coupling to a patient;
a measuring circuit that measures an electrical parameter of the patient via the electrodes; and a processor to select a dosage based on an age-related classification of the patient and the measured electrical parameter, and control delivery of electrotherapy at the selected dosage to the patient via the electrodes, wherein the processor selects a dosage by identifying a nominal dosage and adjusting the nominal dosage based on the age-related classification and the measured electrical parameter, and wherein the processor adjusts the nominal dosage to provide a first probability of successful electrotherapy for the patient based on the measured electrical parameter that is substantially equivalent to a second probability of successful electrotherapy provided by the nominal dosage based on an average value for the electrical parameter that corresponds to the age-related classification of the patient.

45. A device comprising:

a set of electrodes for coupling to a patient;

a measuring circuit that measures an electrical parameter of the patient via the electrodes; and a processor to select a dosage based on an age-related classification of the patient and the measured electrical parameter, and control delivery of electrotherapy at the selected dosage to the patient via the electrodes, wherein the processor selects a dosage by identifying a nominal dosage and adjusting the nominal dosage based on the age-related classification and the measured electrical parameter, and wherein the processor adjusts the nominal dosage by adjusting the nominal dosage to an adjusted dosage that is greater than the nominal dosage if the measured electrical parameter is greater than an average value of the electrical parameter for the age-related classification, less than the nominal dosage if the measured electrical parameter is less than the average value, and equal to the nominal dosage if the measured electrical parameter is equal to the average value.

* * * * *